United States Patent
El-Sherbeini et al.

(10) Patent No.: US 6,890,910 B1
(45) Date of Patent: May 10, 2005

(54) MURD PROTEIN AND GENE OF PSEUDOMONAS AERUGINOSA

(75) Inventors: Mohammed El-Sherbeini, Westfield, NJ (US); Barbara Azzolina, Denville, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/701,229

(22) PCT Filed: May 26, 1999

(86) PCT No.: PCT/US99/11585

§ 371 (c)(1), (2), (4) Date: Aug. 23, 2001

(87) PCT Pub. No.: WO99/61050

PCT Pub. Date: Dec. 2, 1999

Related U.S. Application Data
(60) Provisional application No. 60/087,308, filed on May 29, 1998.

(51) Int. Cl.[7] ............................................... A61K 48/00
(52) U.S. Cl. ..................... 514/44; 536/23.1; 536/23.2; 536/23.4; 536/23.7; 530/350; 435/69.1; 435/252.3; 435/254.11; 435/325; 435/320.1; 435/455; 435/471; 514/459
(58) Field of Search ................... 514/44, 459, 460; 435/69.1, 252.3, 254.11, 325, 320.1, 455, 471, 172.3, 41, 70.1; 536/23.1, 23.2, 23.4, 23.7; 530/350

(56) References Cited

U.S. PATENT DOCUMENTS

| | | | | |
|---|---|---|---|---|
| 5,681,694 A | * | 10/1997 | Hoskins et al. | ................. 435/4 |
| 5,834,270 A | * | 11/1998 | Hoskins et al. | ............. 435/488 |
| 5,929,045 A | * | 7/1999 | Wallis et al. | ................. 514/44 |
| 6,211,161 B1 | * | 4/2001 | Beattie et al. | ................ 514/44 |
| 6,350,598 B1 | * | 2/2002 | Wallis et al. | ............... 435/183 |
| 6,506,581 B1 | * | 1/2003 | Fleischmann et al. | ..... 435/69.1 |
| 6,534,278 B1 | * | 3/2003 | Rothstein | .................... 435/7.2 |
| 6,534,284 B1 | * | 3/2003 | El-Sherbeini et al. | ...... 435/69.1 |
| 6,551,795 B1 | * | 4/2003 | Rubenfield et al. | ........ 435/69.1 |
| 6,746,858 B1 | * | 6/2004 | El-Sherbeini et al. | ....... 435/183 |

\* cited by examiner

*Primary Examiner*—L. F. Smith
*Assistant Examiner*—Ginny Allen Portner
(74) *Attorney, Agent, or Firm*—Michael D. Yablonsky; Jack L. Tribble

(57) ABSTRACT

This invention provides isolated polynucleotides that encode the MurD protein of *Pseudomonas aeruginosa*. Purified and isolated MurD recombinant proteins are also provided. Nucleic acid sequences which encode functionally active MurD proteins are described. Assays for the identification of modulators of the of expression of murD and inhibitors of the activity of MurD, are also provided.

5 Claims, 2 Drawing Sheets

```
ATGAGCCTGATCGCCTCCGACCACTTCCGCATCGTTGTCGGCCTCGGCAAGAGCGGCATG
MetSerLeuIleAlaSerAspHisPheArgIleValValGlyLeuGlyLysSerGlyMet

TCCCTGGTGCGCTACCTGGCGCGCCGCGGCTTGCCTTTCGCCGTGGTCGATACCCGAGAG
SerLeuValArgTyrLeuAlaArgArgGlyLeuProPheAlaValValAspThrArgGlu

AACCCGCCGGAGCTGGCCCACCCTGCGTGCCCAGTATCCGCAGGTGGAAGTGCGTTGCGGC
AsnProProGluLeuAlaThrLeuArgAlaGlnTyrProGlnValGluValArgCysGly

GAACTCGACGCCGAGTTCCTCTGCTCCGCCCGCGAACTCTATGTCAGCCCCGGCTTGTCG
GluLeuAspAlaGluPheLeuCysSerAlaArgGluLeuTyrValSerProGlyLeuSer

CTGCGCACCCCTGCGCTGGTACAGGCCGCGCGAAAGGCGTGCGCATCTCCGGTGACATC
LeuArgThrProAlaLeuValGlnAlaAlaAlaLysGlyValArgIleSerGlyAspIle

GATCTCTTCGCCCGCGAGGCGAAGGCCCCGATCGTCGCCATCACCGGTTCCAACGCGAAG
AspLeuPheAlaArgGluAlaLysAlaProIleValAlaIleThrGlySerAsnAlaLys

AGCACCGTGACCACCCTGGTGGGCGAAATGGCGGTGGCCGCGGACAAGCGTGTCGCCGTC
SerThrValThrThrLeuValGlyGluMetAlaValAlaAlaAspLysArgValAlaVal

GGCGGCAACCTCGGCACCCCGGCGCTCGACCTGCTGGCCGACGACATCGAGCTGTACGTG
GlyGlyAsnLeuGlyThrProAlaLeuAspLeuLeuAlaAspAspIleGluLeuTyrVal

TTGGAGCTGTCGAGCTTCCAGCTGGAAACCTGCGATCGCCTCAACGCCGAGGTGGCGACC
LeuGluLeuSerSerPheGlnLeuGluThrCysAspArgLeuAsnAlaGluValAlaThr

GTGCTGAACGTCAGCGAAGACCATATGGATCGCTACGACGGCATGGCTGACTACCACCTG
ValLeuAsnValSerGluAspHisMetAspArgTyrAspGlyMetAlaAspTyrHisLeu

GCCAAGCACCGGATCTTCCGCGGTGCCCGCCAGGTCGTGGTGAATCGCGCCGATGCCCTG
AlaLysHisArgIlePheArgGlyAlaArgGlnValValValAsnArgAlaAspAlaLeu
```

(SEQ ID NO:1, positions 51-710)
(SEQ ID NO:2, positions 1-220)

```
ATGAGCCTGATCGCCTCCGACCACTTCCGCATCGTTGTCGGCCTCGGCAAGAGCGGCATG
MetSerLeuIleAlaSerAspHisPheArgIleValValGlyLeuGlyLysSerGlyMet

TCCCTGGTGCGCTACCTGGCGCGCCGCGGCTTGCCTTTCGCCGTGGTCGATACCCGAGAG
SerLeuValArgTyrLeuAlaArgArgGlyLeuProPheAlaValValAspThrArgGlu

AACCCGCCGGAGCTGGCCACCCTGCGTGCCCAGTATCCGCAGGTGGAAGTGCGTTGCGGC
AsnProProGluLeuAlaThrLeuArgAlaGlnTyrProGlnValGluValArgCysGly

GAACTCGACGCCGAGTTCCTCTGCTCCGCCCGCGAACTCTATGTCAGCCCCGGCTTGTCG
GluLeuAspAlaGluPheLeuCysSerAlaArgGluLeuTyrValSerProGlyLeuSer

CTGCGCACCCCTGCGCTGGTACAGGCCGCCGCGAAAGGCGTGCGCATCTCCGGTGACATC
LeuArgThrProAlaLeuValGlnAlaAlaAlaLysGlyValArgIleSerGlyAspIle

GATCTCTTCGCCCGCGAGGCGAAGGCCCCGATCGTCGCCATCACCGGTTCCAACGCGAAG
AspLeuPheAlaArgGluAlaLysAlaProIleValAlaIleThrGlySerAsnAlaLys

AGCACCGTGACCACCCTGGTGGGCGAAATGGCGGTGGCCGCGGACAAGCGTGTCGCCGTC
SerThrValThrThrLeuValGlyGluMetAlaValAlaAlaAspLysArgValAlaVal

GGCGGCAACCTCGGCACCCCGGCGCTCGACCTGCTGGCCGACGACATCGAGCTGTACGTG
GlyGlyAsnLeuGlyThrProAlaLeuAspLeuLeuAlaAspAspIleGluLeuTyrVal

TTGGAGCTGTCGAGCTTCCAGCTGGAAACCTGCGATCGCCTCAACGCCGAGGTGGCGACC
LeuGluLeuSerSerPheGlnLeuGluThrCysAspArgLeuAsnAlaGluValAlaThr

GTGCTGAACGTCAGCGAAGACCATATGGATCGCTACGACGGCATGGCTGACTACCACCTG
ValLeuAsnValSerGluAspHisMetAspArgTyrAspGlyMetAlaAspTyrHisLeu

GCCAAGCACCGGATCTTCCGCGGTGCCCGCCAGGTCGTGGTGAATCGCGCCGATGCCCTG
AlaLysHisArgIlePheArgGlyAlaArgGlnValValValAsnArgAlaAspAlaLeu
```

(SEQ ID NO:1, positions 51-710)
(SEQ ID NO:2, positions 1-220)

FIG.1A

```
ACCCGACCGCTGATCGCCGATACCGTGCCGTGCTGGTCGTTCGGCCTGAACAAGCCGGAC
ThrArgProLeuIleAlaAspThrValProCysTrpSerPheGlyLeuAsnLysProAsp

TTCAAGGCTTTCGGCCTGATCGAGGAAGACGGCCAGAAGTGGCTGGCGTTCCAGTTCGAC
PheLysAlaPheGlyLeuIleGluGluAspGlyGlnLysTrpLeuAlaPheGlnPheAsp

AAGCTGCTGCCGGTTGGCGAACTGAAGATCCGTGGCGCCCACAACTATTCCAACGCGCTC
LysLeuLeuProValGlyGluLeuLysIleArgGlyAlaHisAsnTyrSerAsnAlaLeu

GCCGCGCTGGCGCTGGGCCATGCGGTCGGCCTGCCGTTCGACGCCATGCTCGGCGCGCTG
AlaAlaLeuAlaLeuGlyHisAlaValGlyLeuProPheAspAlaMetLeuGlyAlaLeu

AAGGCGTTTTCCGGCCTGGCTCATCGCTGCCAGTGGGTACGCGAGCGGCAGGGCGTGAGC
LysAlaPheSerGlyLeuAlaHisArgCysGlnTrpValArgGluArgGlnGlyValSer

TACTACGACGATTCCAAGGCCACCAACGTCGGCGCCGCCCTGGCGGCGATCGAGGGGCTG
TyrTyrAspAspSerLysAlaThrAsnValGlyAlaAlaLeuAlaAlaIleGluGlyLeu

GGTGCCGACATCGACGGCAAGCTGGTGCTGCTCGCCGGCGGAGACGGCAAGGGCGCCGAT
GlyAlaAspIleAspGlyLysLeuValLeuLeuAlaGlyGlyAspGlyLysGlyAlaAsp

TTCCATGACCTGCGCGAGCCGGTCGCGCGCTTCTGCCGGGCGGTGGTACTGCTTGGCCGT
PheHisAspLeuArgGluProValAlaArgPheCysArgAlaValValLeuLeuGlyArg

GACGCCGGGCTGATTGCCCAGGCACTGGGCAACGCGGTACCGCTGGTGCGCGTCGCAACG
AspAlaGlyLeuIleAlaGlnAlaLeuGlyAsnAlaValProLeuValArgValAlaThr

CTGGACGAAGCAGTCCGGCAGGCCGCCGAGCTGGCCCGCGAAGGCGATGCGGTGCTGTTG
LeuAspGluAlaValArgGlnAlaAlaGluLeuAlaArgGluGlyAspAlaValLeuLeu

TCGCCGGCCTGCGCGAGCCTGGACATGTTCAAGAACTTCGAAGAACGCGGACGCCTGTTC
SerProAlaCysAlaSerLeuAspMetPheLysAsnPheGluGluArgGlyArgLeuPhe

GCCAAAGCCGTAGAGGAGCTAGCGTGA (SEQ ID NO:1, positions 711-1397)
AlaLysAlaValGluGluLeuAlaEnd (SEQ ID NO:2, positions 221-448)
```

FIG. 1B

SEQUENCE LISTING

```
<160> NUMBER OF SEQ ID NOS: 4

<210> SEQ ID NO 1
<211> LENGTH: 1450
<212> TYPE: DNA
<213> ORGANISM: Pseudomonas aeruginosa

<400> SEQUENCE: 1
cgtgctgatc ggcctcgcca ccttgaagct gcgttgagga cgaagagagc atgagcctga      60
tcgcctccga ccacttccgc atcgttgtcg gcctcggcaa gagcggcatg tccctggtgc     120
gctacctggc gcgccgcggc ttgccttccg ccgtggtcga tacccgagag aacccgccgg     180
agctggccac cctgcgtgcc cagtatccgc aggtggaagt gcgttgcggc gaactcgacg     240
ccgagttcct ctgctccgcc cgcgaactct atgtcagccc cggcttgtcg ctgcgcaccc     300
ctgcgctggt acaggccgcc gcgaaaggcg tgcgcatctc cggtgacatc gatctcttcg     360
cccgcgaggc gaaggccccg atcgtcgcca tcaccggttc caacgcgaag agcaccgtga     420
ccaccctggt gggcgaaatg gcggtggccg cggacaagcg tgtcgccgtc ggcggcaacc     480
tcggcacccc ggcgctcgac ctgctggccg acgacatcga gctgtacgtg ttggagctgt     540
cgagcttcca gctggaaacc tgcgatcgcc tcaacgccga ggtggcgacc gtgctgaacg     600
tcagcgaaga ccatatggat cgctacgacg gcatggctga ctaccacctg gccaagcacc     660
ggatcttccg cggtgcccgc caggtcgtgg tgaatcgcgc cgatgccctg acccgaccgc     720
tgatcgccga taccgtgccg tgctggtcgt tcggcctgaa caagccggac ttcaaggctt     780
tcggcctgat cgaggaagac ggccagaagt ggctggcgtt ccagttcgac aagctgctgc     840
cggttggcga actgaagatc cgtggcgccc acaactattc caacgcgctc gccgcgctgg     900
cgctgggcca tgcggtcggc ctgccgttcg acgccatgct cggcgcgctg aaggcgtttt     960
```

-continued

```
ccggcctggc tcatcgctgc cagtgggtac gcgagcggca gggcgtgagc tactacgacg    1020
attccaaggc caccaacgtc ggcgccgccc tggcggcgat cgaggggctg ggtgccgaca    1080
tcgacggcaa gctggtgctg ctcgccggcg gagacggcaa gggcgccgat ttccatgacc    1140
tgcgcgagcc ggtcgcgcgc ttctgccggg cggtggtact gcttggccgt gacgccgggc    1200
tgattgccca ggcactgggc aacgcggtac cgctggtgcg cgtcgcaacg ctggacgaag    1260
cagtccggca ggccgccgag ctggcccgcg aaggcgatgc ggtgctgttg tcgccggcct    1320
gcgcgagcct ggacatgttc aagaacttcg aagaacgcgg acgcctgttc gccaaagccg    1380
tagaggagct agcgtgatgc tgtcggtgtt gcgccccttc ccgtcgccgc tgttgagccg    1440
gcacggcatc                                                          1450
```

<210> SEQ ID NO 2
<211> LENGTH: 448
<212> TYPE: PRT
<213> ORGANISM: Pseudomonas aeruginosa

<400> SEQUENCE: 2

```
Met Ser Leu Ile Ala Ser Asp His Phe Arg Ile Val Val Gly Leu Gly
 1               5                  10                  15

Lys Ser Gly Met Ser Leu Val Arg Tyr Leu Ala Arg Arg Gly Leu Pro
            20                  25                  30

Phe Ala Val Val Asp Thr Arg Glu Asn Pro Pro Glu Leu Ala Thr Leu
        35                  40                  45

Arg Ala Gln Tyr Pro Gln Val Glu Val Arg Cys Gly Glu Leu Asp Ala
    50                  55                  60

Glu Phe Leu Cys Ser Ala Arg Glu Leu Tyr Val Ser Pro Gly Leu Ser
65                  70                  75                  80

Leu Arg Thr Pro Ala Leu Val Gln Ala Ala Lys Gly Val Arg Ile
                85                  90                  95

Ser Gly Asp Ile Asp Leu Phe Ala Arg Glu Ala Lys Ala Pro Ile Val
            100                 105                 110

Ala Ile Thr Gly Ser Asn Ala Lys Ser Thr Val Thr Thr Leu Val Gly
        115                 120                 125

Glu Met Ala Val Ala Ala Asp Lys Arg Val Ala Val Gly Gly Asn Leu
    130                 135                 140

Gly Thr Pro Ala Leu Asp Leu Leu Ala Asp Asp Ile Glu Leu Tyr Val
145                 150                 155                 160

Leu Glu Leu Ser Ser Phe Gln Leu Glu Thr Cys Asp Arg Leu Asn Ala
                165                 170                 175

Glu Val Ala Thr Val Leu Asn Val Ser Glu Asp His Met Asp Arg Tyr
            180                 185                 190

Asp Gly Met Ala Asp Tyr His Leu Ala Lys His Arg Ile Phe Arg Gly
        195                 200                 205

Ala Arg Gln Val Val Val Asn Arg Ala Asp Ala Leu Thr Arg Pro Leu
    210                 215                 220

Ile Ala Asp Thr Val Pro Cys Trp Ser Phe Gly Leu Asn Lys Pro Asp
225                 230                 235                 240

Phe Lys Ala Phe Gly Leu Ile Glu Glu Asp Gly Gln Lys Trp Leu Ala
                245                 250                 255

Phe Gln Phe Asp Lys Leu Leu Pro Val Gly Glu Leu Lys Ile Arg Gly
            260                 265                 270

Ala His Asn Tyr Ser Asn Ala Leu Ala Ala Leu Ala Leu Gly His Ala
```

```
                      275                 280                 285
Val Gly Leu Pro Phe Asp Ala Met Leu Gly Ala Leu Lys Ala Phe Ser
    290                 295                 300

Gly Leu Ala His Arg Cys Gln Trp Val Arg Glu Arg Gln Gly Val Ser
305                 310                 315                 320

Tyr Tyr Asp Asp Ser Lys Ala Thr Asn Val Gly Ala Ala Leu Ala Ala
                325                 330                 335

Ile Glu Gly Leu Gly Ala Asp Ile Asp Gly Lys Leu Val Leu Leu Ala
                340                 345                 350

Gly Gly Asp Gly Lys Gly Ala Asp Phe His Asp Leu Arg Glu Pro Val
                355                 360                 365

Ala Arg Phe Cys Arg Ala Val Val Leu Leu Gly Arg Asp Ala Gly Leu
    370                 375                 380

Ile Ala Gln Ala Leu Gly Asn Ala Val Pro Leu Val Arg Val Ala Thr
385                 390                 395                 400

Leu Asp Glu Ala Val Arg Gln Ala Ala Glu Leu Ala Arg Glu Gly Asp
                405                 410                 415

Ala Val Leu Leu Ser Pro Ala Cys Ala Ser Leu Asp Met Phe Lys Asn
                420                 425                 430

Phe Glu Glu Arg Gly Arg Leu Phe Ala Lys Ala Val Glu Glu Leu Ala
                435                 440                 445
```

<210> SEQ ID NO 3
<211> LENGTH: 25
<212> TYPE: DNA
<213> ORGANISM: Pseudomonas aeruginosa

<400> SEQUENCE: 3
ttctcgagat gagcctgatc gcctc                                              25

<210> SEQ ID NO 4
<211> LENGTH: 26
<212> TYPE: DNA
<213> ORGANISM: Pseudomonas aeruginosa

<400> SEQUENCE: 4
ttggatcctc acgctagctc ctctac                                             26

MURD PROTEIN AND GENE OF *PSEUDOMONAS AERUGINOSA*

CROSS-REFERENCE TO RELATED APPLICATIONS

This application claims the benefit of U.S. Provisional Application 60/087,308, filed May 29, 1998, now abandoned, and is a 371 of PCT Application US99/11585, filed May 26, 1999.

FIELD OF THE INVENTION

This invention relates to the genes and enzymes involved in cell wall synthesis in bacteria, and particularly to the inhibition of such enzymes.

BACKGROUND OF THE INVENTION

The molecular target of many naturally-occurring antibiotics, including fosfomycin, cycloserine and β-lactams, is the synthesis of the bacterial cell wall. The frequency with which these types of antibiotics arose in evolution indicates that the pathway of cell wall biosynthesis is a particularly effective point of attack against bacteria. Genetic studies confirm the soundness of this process as a target, as temperature-sensitive alleles of the intracellular pathway genes are lytic, and therefore lethal. Since the building blocks of the cell wall are highly conserved structures in both Gram-positive and Gram-negative bacteria, but are unique to the *eubacteria*, novel inhibitors of cell wall formation are expected to be both broad spectrum and safe antibiotics.

The bacterial cell wall is a polymer, a single molecule composed of peptidoglycan that defines the boundary and shape of the cell. Assembled by crosslinking glycan chains with short peptide bridges (Rogers, H. J., H. R. Perkins, and J. B. Ward, 1980, Biosynthesis of peptidoglycan. p. 239–297. In Microbial cell walls and membranes. Chapman & Hall Ltd. London), the completed structure is strong enough to maintain cell integrity against an osmotic pressure differential of over four atmospheres, but also flexible enough to allow the cell to move, grow and divide.

The construction of the peptidoglycan begins in the cytoplasm with an activated sugar molecule, UDP-N-acetylglucosamine. After two reactions (catalyzed by MurA and MurB) that result in the placement of a lactyl group on the 3-OH of the glucosamine moiety, a series of ATP-dependent amino acid ligases (MurC, -D, -E, and -F) catalyze the stepwise synthesis of the pentapeptide sidechain using the newly synthesized lactyl carboxylate as the first acceptor site. After attachment of the sugar pentapeptide to a lipid carrier in the plasma membrane, another glucosamine unit is added to the 4-OH of the muramic acid moiety. The completed monomeric building block is moved across the membrane into the periplasm where the penicillin-binding proteins enzymatically add it into the growing cell wall (Lugtenberg, E. J. J., 1972, Studies on *Escherichia coli* enzymes involved in the synthesis of Uridine Diphosphate-N-Acetyl-Muramyl-pentapeptide. J. Bacteriol. 110:26–34; Mengin-Lecreulx, D., B. Flouret, and J. van Heijenoort, 1982, Cytoplasmic steps of peptidoglycan synthesis in *Escherichia coli*. J. Bacteriol. 151: 1109–1117).

Because the pentapeptide sidechain is not synthesized ribosomally it contains more diverse chemical functionality than a typical peptide, both structurally and stereochemically. Two of the enzymes catalyze the addition of D-amino acids (MurD and MurF) and MurE mediates the formation of a peptide bond between the g-carboxylate of D-glutamate and the amino group of L-lysine. Presumably these structures render the exposed peptidoglycan resistant to the action of proteases, but they also imply that the active sites of the enzymes must have unusual structures in order to handle the somewhat uncommon substrates. These unusual active sites are targets to bind novel inhibitors that can have antimicrobial activity.

Among these potential enzyme targets is MurD. The first partial purification and characterization of a D-glutamate-adding enzyme was from *Staphlococcus aureus* (Ito, E. and J. L. Strominger, 1962. Enzymatic synthesis of the peptide in bacterial uridine nucleotides: Enzymatic addition of L-alanine, D-glutamic acid, and L-lysine. J. Biol. Chem. 237: 2689–2695; Nathenson, S. G., J. L. Strominger, and E. Ito, 1964. Enzymatic synthesis of the peptide in bacterial uridine nucleotides: purification and properties of D-Glutamic acid-adding enzyme, J. Biol. Chem. 239: 1773–1776), followed by studies in more detail on the isolated *Eschericia coli* enzyme (Blanot, D., A. Kretsovali, M. Abo-Ghalia, D. Mengin-Lecreulx, and J. van Heijenoort, 1983. Synthesis of analogues of precusors of bacterial peptidoglycan. In Peptides. Blaha, K. and P. Malon, eds. pp. 311–314, Walter de Gryter and Co. Berlin, N.Y.; Jin, H., Emanuele, J. J., Jr., Fairman, R., Robertson, J. G., Hail, M. E., Ho, H.-T., Falk, P. and Villafranca, J. J., 1996. Structural studies of *Escherichia coli* UDP-N-acetylmuramate: L-alanine ligase. Biochemistry 35: 14423–14431; Ito E. and J. L. Strominger, 1973. Enzymatic synthesis of the peptide in bacterial uridine nucleotides: Comparative biochemistry. J. Biol. Chem. 248: 3131–3136; Michaud, C. D. Blanot, B. Flouret, and J. van Heijenoort, 1987. Partial purification and specificity studies of the D-glutamate-adding and D-alanyl-D-alanine-adding enzymes from *Escherichia coli* K12. Eur. J. Biochem. 166: 631–637). A purified recombinant *E. coli* MurD was reported (Pratviel-Sosa F, D. Mengin-Lecreulx and J. van Heijenoort, 1991. Over-production, purification and properties of the uridine diphosphate N-acetylmuramoyl-L-alanine:D-glutamate ligase from *Escherichia coli*. Eur. J. Biochem. 202 (3):1169–1176) and genes encoding MurD have been cloned from several species of bacteria including *E. coli* (Ikeda, M., M. Wachi, F. Ishino, and M. Matsuhashi, 1990a. Nucleotide sequence involving murD and an open reading frame ORF-Y spacing murF and ftsW in *Escherichia coli*. Nucleic Acids Res. 18:1058; Mengin-Lecreulx, D., C Parquet, L. Desviat, J. Pla, B. Flouret, J. Ayala and J. van Heijenoort, 1989. Organization of the murE-murG region of *Escherichia coli*: Identification of the murD gene encoding the D-glutamic-acid-adding enzyme. J. Bacteriol. 171: 6126–6134) and *Bacilus subtilis* (Daniel, R. A., and J. Errington, 1993. DNA sequence of the murE-murD region of *Bacillus subtilis* 168. J. Gen. Microbiol. 139:361–370; Henriques, A. O. de Lencaster, H. and P. J. Piggot, 1992, A *Bacillus subtilis* morphogene cluster that includes spoVE is homologous to the mra region of *Escherichia coli*. Biochimie. 74: 735–748). More recently, Purified recombinant MurD enzymes were purified from Gram-positive cocci (El-Sherbeini, M., Geissler, W., Pittman, J., Yuan, X., Wong, K. K. and Pompliano, D. L. 1998, Cloning and expression of *Staphylococcus aureus* and *Streptococcus pyogenes* murD genes encoding uri dine diphosphate N-acetylmuramoyl-L-alanine:D-glutamate ligases. Gene, 210: 117–125).

Compounds have been designed and synthesized that have inhibitory activity against the *E. coli* enzyme (Tanner, M. E., S. Vaganay, van Heijenoort, J., and D. Blanot, 1996. Phosphinate Inhibitors of the D-Glutamic Acid-Adding Enzyme of Peptidoglycan Biosynthesis. J. Org. Chem. 61: 1756–1760), although they do not have antibacterial activity.

SUMMARY OF THE INVENTION

Polynucleotides and polypeptides of *Pseudomonas aeruginosa* MurD, an enzyme involved in bacterial cell wall biosynthesis are provided. The recombinant MurD enzyme is catalytically active in ATP-dependent D-glutamate addition reactions. The enzyme is used in in vitro assays to screen for antibacterial compounds that target cell wall biosynthesis. The invention includes the purified polynucleotides, purified proteins encoded by the polynucleotides, and host cells expressing the recombinant enzyme, probes and primers, and the use of these molecules in assays.

An aspect of this invention is a polynucleotide having a sequence encoding a *Pseudomonas aeruginosa* MurD protein, or a complementary sequence. In a particular embodiment the encoded protein has a sequence corresponding to SEQ ID NO:2. In other embodiments, the encoded protein can be a naturally occurring mutant or polymorphic form of the protein. In preferred embodiments the polynucleotide can be DNA, RNA or a mixture of both, and can be single or double stranded. In particular embodiments, the polynucelotide is comprised of natural, non-natural or modified nucleotides. In some embodiments, the internucleotide linkages are linkages that occur in nature. In other embodiments, the internucleotide linkages can be non-natural linkages or a mixture of natural and non-natural linkages. In a most preferred embodiment, the polynucleotide has a sequence shown in SEQ ID NO:1.

An aspect of this invention is a polynucleotide having a sequence of at least about 25 contiguous nucleotides that is specific for a naturally occurring polynucleotide encoding a *Pseudomonas aeruginosa* MurD protein. In particular preferred embodiments, the polynucleotides of this aspect are useful as probes for the specific detection of the presence of a polynucleotide encoding a *Pseudomonas aeruginosa* MurD protein. In other particular embodiments, the polynucleotides of this aspect are useful as primers for use in nucleic acid amplification based assays for the specific detection of the presence of a polynucleotide encoding a *Pseudomonas aeruginosa* MurD protein. In preferred embodiments, the polynucleotides of this aspect can have additional components including, but not limited to, compounds, isotopes, proteins or sequences for the detection of the probe or primer.

An aspect of this invention is an expression vector including a polynucleotide encoding a *Pseudomonas aeruginosa* MurD protein, or a complementary sequence, and regulatory regions. In a particular embodiment the encoded protein has a sequence corresponding to SEQ ID NO:2. In particular embodiments, the vector can have any of a variety of regulatory regions known and used in the art as appropriate for the types of host cells the vector can be used in. In a most preferred embodiment, the vector has regulatory regions appropriate for the expression of the encoded protein in gram-negative prokaryotic host cells. In other embodiments, the vector has regulatory regions appropriate for expression of the encoded protein in grain-positive host cells, yeasts, cyanobacteria or actinomycetes. In some preferred embodiments the regulatory regions provide for inducible expression while in other preferred embodiments the regulatory regions provide for constitutive expression. Finally, according to this aspect, the expression vector can be derived from a plasmid, phage, virus or a combination thereof.

An aspect of this invention is host cell comprising an expression vector including a polynucleotide encoding a *Pseudomonas aeruginosa* MurD protein, or a complementary sequence, and regulatory regions. In a particular embodiment the encoded protein has a sequence corresponding to SEQ ID NO:2. In preferred embodiments, the host cell is a yeast, gram-positive bacterium, cyanobacterium or actinomycete. In a most preferred embodiment, the host cell is a gram-negative bacterium.

An aspect of this invention is a process for expressing a MurD protein of *P. aeruginosa* in a host cell. In this aspect a host cell is transformed or transfected with an expression vector including a polynucleotide encoding a *Pseudomonas aeruginosa* MurD protein, or a complementary sequence. According to this aspect, the host cell is cultured under conditions conducive to the expression of the encoded MurD protein. In particular embodiments the expression is inducible or constitutive. In a particular embodiment the encoded protein has a sequence corresponding to SEQ ID NO:2.

An aspect of this invention is a purified polypeptide having an amino acid sequence of SEQ ID NO:2 or the sequence of a naturally occurring mutant or polymorphic form of the protein.

An aspect of this invention is a method of determining whether a candidate compound can inhibit the activity of a *P. aeruginosa* MurD polypeptide. According to this aspect a polynucleotide encoding the polypeptide is used to construct an expression vector appropriate for a particular host cell. The host cell is transformed or transfected with the expression vector and cultured under conditions conducive to the expression of the MurD polypeptide. The cell is contacted with the candidate. Finally, one measures the activity of the MurD polypeptide in the presence of the candidate. If the activity is lower relative to the activity of the protein in the absence of the candidate, then the candidate is a inhibitor of the MurD polypeptide. In preferred embodiments, the polynucleotide encodes a protein having an amino acid sequence of SEQ ID NO:2 or a naturally occurring mutant of polymorphic form thereof. In other preferred embodiments, the polynucleotide has the sequence of SEQ ID NO:1. In particular embodiments, the relative activity of MurD is determined by comparing the activity of the MurD in a host cell. In some embodiments, the host cell is disrupted and the candidate is contacted to the released cytosol. In other embodiments, the cells can be disrupted contacting with the candidate and before determining the activity of the MurD protein. Finally, according to this aspect the relative activity can determined by comparison to a previously measured or expected activity value for the MurD activity in the host under the conditions. However, in preferred embodiments, the relative activity is determined by measuring the activity of the Mur D in a control cell that was not contacted with a candidate compound. In particular embodiments, the host cell is a pseudomonad and the protein inhibited is the MurD produced by the pseudomonad.

An aspect of this invention is a compound that is an inhibitor of a *P. aeruginosa* MurD protein an assay described herein. In preferred embodiments, the compound is an inhibitor of a *P. aeruginosa* MurD protein produced by a host cell comprising an expression vector of this invention. In most preferred embodiments, the compound is also an inhibitor of MurD protein produced by a pathogenic strain *P. aeruginosa* and also inhibits the growth of said pseudomonad.

An aspect of this invention is a pharmaceutical preparation that includes an inhibitor of *P. aeruginosa* MurD and a pharmaceutically acceptable carrier.

An aspect of this invention is a method of treatment comprising administering a inhibitor of the *P. aeruginosa* MurD to a patient. The treatment can be prophylactic or therapeutic. In preferred embodiments, the appropriate dosage for a particular patient is determined by a physician.

By "about" it is meant within approximately 10–20% greater or lesser than particularly stated.

As used herein an "inhibitor" is a compound that interacts with and inhibits or prevents a polypeptide of MurD from catalyzing the ATP-dependent addition of D-glutamate to an alanyl residue of the UDP-N-acetylmuramyl-L-alanine precursor.

As used herein a "modulator" is a compound that interacts with an aspect of cellular biochemistry to effect an increase or decrease in the amount of a polypeptide of MurD present in, at the surface or in the periplasm of a cell, or in the surrounding serum or media. The change in amount of the MurD polypeptide can be mediated by the effect of a modulator on the expression of the protein, e.g., the transcription, translation, post-translational processing, translocation or folding of the protein, or by affecting a component(s) of cellular biochemistry that directly or indirectly participates in the expression of the protein. Alternatively, a modulator can act by accelerating or decelerating the turnover of the protein either by direct interaction with the protein or by interacting with another component(s) of cellular biochemistry which directly or indirectly effects the change.

All of the references cited herein are incorporated by reference in their entirety as background material.

BRIEF DESCRIPTION OF THE DRAWINGS

FIGS. 1A & 1B. Nucleotide sequence (SEQ ID NO: 1) and the predicted amino acid sequence (SEQ ID NO:2) of *P. aeruginosa* murD. The amino acid sequence (SEQ ID NO:2) is presented in three-letter code below the nucleotide sequence (nucleotides 51 to 1395 of SEQ ID NO: 1).

DETAILED DESCRIPTION OF THE INVENTION

This invention provides polynucleotides and polypeptides of a cell wall biosynthesis gene from *Pseudomonas aeruginosa*, referred to herein as MurD. The polynucleotides and polypeptides are used to further provide expression vectors, host cells comprising the vectors, probes and primers, antibodies against the MurD protein and polypeptides thereof, assays for the presence or expression of MurD and assays for the identification of modulators and inhibitors of MurD.

Bacterial MurD, UDP-N-acetylmuramyl-L-alanine:D-glutamate ligase, a cytoplasmic peptidoglycan biosynthetic enzyme, catalyzes the ATP-dependent addition of D-glutamate to an alanyl residue of the UDP-N-acetylmuramyl-L-alanine precursor, generating the dipeptide.

The murD gene was cloned from *Pseudomonas aeruginosa*. Sequence analysis of the *P. aeruginosa* murD gene revealed an open reading frame of 448 amino acids. The deduced amino acid sequence of *P. aeruginosa* MurD is homologous to MurD from *Escherichia coli, Haemophilus influenza, Bacillus subtilis* and *S. aureus*. Recombinant MurD protein from *P. aeruginosa* was over-produced as His-tagged fusion protein in *Escherichia coli* host cells. The *P. aeruginosa* MurD enzyme was purified to apparent homogeneity. The recombinant enzyme catalyzed the ATP-dependent addition of D-glutamate to the precursor sugar peptide.

Nucleic acids encoding murD from *Pseudomonas aeruginosa* are useful in the expression and production of the *P. aeruginosa* MurD protein. The nucleic acids are also useful in providing probes for detecting the presence of *P. aeruginosa*.

Polynucleotides

A preferred aspect of the present invention is an isolated nucleic acid encoding a MurD protein of *Pseudomonas aeruginosa*. A preferred embodiment is a nucleic acid having the sequence disclosed in FIG. 1, SEQ ID NO: 1 and disclosed as follows:

```
CGTGCTGATC GGCCTCGCCA CCTTGAAGCT GCGTTGAGGA CGAAGAGAGC (SEQ ID NO:1)

ATGAGCCTGA TCGCCTCCGA CCACTTCCGC ATCGTTGTCG GCCTCGGCAA

GAGCGGCATG TCCCTGGTGC GCTACCTGGC GCGCCGCGGC TTGCCTTTCG

CCGTGGTCGA TACCCGAGAG AACCCGCCGG AGCTGGCCAC CCTGCGTGCC

CAGTATCCGC AGGTGGAAGT GCGTTGCGGC GAACTCGACG CCGAGTTCCT

CTGCTCCGCC CGCGAACTCT ATGTCAGCCC CGGCTTGTCG CTGCGCACCC

CTGCGCTGGT ACAGGCCGCC GCGAAAGGCG TGCGCATCTC CGGTGACATC

GATCTCTTCG CCCGCGAGGC GAAGGCCCCG ATCGTCGCCA TCACCGGTTC

CAACGCGAAG AGCACCGTGA CCACCCTGGT GGGCGAAATG GCGGTGGCCG

CGGACAAGCG TGTCGCCGTC GGCGGCAACC TCGGCACCCC GGCGCTCGAC

CTGCTGGCCG ACGACATCGA GCTGTACGTG TTGGAGCTGT CGAGCTTCCA

GCTGGAAACC TGCGATCGCC TCAACGCCGA GGTGGCGACC GTGCTGAACG

TCAGCGAAGA CCATATGGAT CGCTACGACG GCATGGCTGA CTACCACCTG

GCCAAGCACC GGATCTTCCG CGGTGCCCGC CAGGTCGTGG TGAATCGCGC

CGATGCCCTG ACCCGACCGC TGATCGCCGA TACCGTGCCG TGCTGGTCGT

TCGGCCTGAA CAAGCCGGAC TTCAAGGCTT TCGGCCTGAT CGAGGAAGAC
```

-continued

```
GGCCAGAAGT GGCTGGCGTT CCAGTTCGAC AAGCTGCTGC CGGTTGGCGA

ACTGAAGATC CGTGGCGCCC ACAACTATTC CAACGCGCTC GCCGCGCTGG

CGCTGGGCCA TGCGGTCGGC CTGCCGTTCG ACGCCATGCT CGGCGCGCTG

AAGGCGTTTT CCGGCCTGGC TCATCGCTGC CAGTGGGTAC GCGAGCGGCA

GGGCGTGAGC TACTACGACG ATTCCAAGGC CACCAACGTC GGCGCCGCCC

TGGCGGCGAT CGAGGGGCTG GGTGCCGACA TCGACGGCAA GCTGGTGCTG

CTCGCCGGCG GAGACGGCAA GGGCGCCGAT TTCCATGACC TGCGCGAGCC

GGTCGCGCGC TTCTGCCGGG CGGTGGTACT GCTTGGCCGT GACGCCGGGC

TGATTGCCCA GGCACTGGGC AACGCGGTAC CGCTGGTGCG CGTCGCAACG

CTGGACGAAG CAGTCCGGCA GGCCGCCGAG CTGGCCCGCG AAGGCGATGC

GGTGCTGTTG TCGCCGGCCT GCGCGAGCCT GGACATGTTC AAGAACTTCG

AAGAACGCGG ACGCCTGTTC GCCAAAGCCG TAGAGGAGCT AGCGTGATGC

TGTCGGTGTT GCGCCCCTTC CCGTCGCCGC TGTTGAGCCG GCACGGCATC
```

The translation initiation and termination codons are underlined.

The isolated nucleic acid molecule of the present invention can include a ribonucleic or deoxyribonucleic acid molecule, which can be single (coding or noncoding strand) or double stranded, as well as synthetic nucleic acid, such as a synthesized, single stranded polynucleotide.

The present invention also relates to recombinant vectors and recombinant hosts, both prokaryotic and eukaryotic, which contain the substantially purified nucleic acid molecules disclosed throughout this specification.

As used herein a "polynucleotide" is a nucleic acid of more than one nucleotide. A polynucleotide can be made up of multiple polynucleotide units that are referred to by description of the unit. For example, a polynucleotide can comprise within its bounds a polynucleotide(s) having a coding sequence(s), a polynucleotide(s) that is a regulatory region(s) and/or other polynucleotide units commonly used in the art.

An "expression vector" is a polynucleotide having regulatory regions operably linked to a coding region such that, when in a host cell, the regulatory regions can direct the expression of the coding sequence. The use of expression vectors is well known in the art. Expression vectors can be used in a variety of host cells and, therefore, the regulatory regions are preferably chosen as appropriate for the particular host cell.

A "regulatory region" is a polynucleotide that can promote or enhance the initiation or termination of transcription or translation of a coding sequence. A regulatory region includes a sequence that is recognized by the RNA polymerase, ribosome, or associated transcription or translation initiation or termination factors of a host cell. Regulatory regions that direct the initiation of transcription or translation can direct constitutive or inducible expression of a coding sequence.

Polynucleotides of this invention contain full length or partial length sequences of the MurD gene sequences disclosed herein. Polynucleotides of this -invention can be single or double stranded. If single stranded, the polynucleotides can be a coding, "sense," strand or a complementary, "antisense," strand. Antisense strands can be useful as modulators of the gene by interacting with RNA encoding the MurD protein. Antisense strands are preferably less than full length strands having sequences unique or specific for RNA encoding the protein.

The polynucleotides can include deoxyribonucleotides, ribonucleotides or mixtures of both. The polynucleotides can be produced by cells, in cell-free biochemical reactions or through chemical synthesis. Non-natural or modified nucleotides, including inosine, methylcytosine, deazaguanosine, etc., can be present. Natural phosphodiester internucleotide linkages can be appropriate. However, polynucleotides can have non-natural linkages between the nucleotides. Non-natural linkages are well known in the art and include, without limitation, methylphosphonates, phosphorothioates, phosphorodithionates, phosphoroamidites and phosphate ester linkages. Dephospho-linkages are also known, as bridges between nucleotides. Examples of these include siloxane, carbonate, carboxymethyl ester, acetamidate, carbamate, and thioether bridges. "Plastic DNA," having, for example, N-vinyl, methacryloxyethyl, methacrylamide or ethyleneimine internucleotide linkages, can be used. "Peptide Nucleic Acid" (PNA) is also useful and resists degradation by nucleases. These linkages can be mixed in a polynucleotide.

As used herein, "purified" and "isolated" are utilized interchangeably to stand for the proposition that the polynucleotide, protein and polypeptide, or respective fragments thereof in question have been removed from the in vivo environment so that they exist in a form or purity not found in nature. Purified or isolated nucleic acid molecules can be manipulated by the skilled artisan, such as but not limited to sequencing, restriction digestion, site-directed mutagenesis, and subcloning into expression vectors for a nucleic acid fragment as well as obtaining the wholly or partially purified protein or protein fragment so as to afford the opportunity to generate polyclonal antibodies, monoclonal antibodies, or perform amino acid sequencing or peptide digestion. Therefore, the nucleic acids claimed herein can be present in whole cells or in cell lysates or in a partially or substantially purified form. It is preferred that the molecule be present at a concentration at least about five-fold to ten-fold higher than that found in nature. A polynucleotide is considered substantially pure if it is obtained purified from cellular components by standard methods at a concentration of at least about 100-fold higher than that found in nature. A polynucleotide is considered essentially pure if it is obtained at a concentration of at least about 1000-fold higher than that found in nature. We most prefer polynucleotides that have been purified to homogeneity, that is, at least 10,000–100,000 fold. A chemically synthesized nucleic acid sequence is considered to be substantially purified when purified from its chemical precursors by the standards stated above.

Polypeptides

A preferred aspect of the present invention is a substantially purified form of the MurD protein from *Pseudomonas aeruginosa*. A preferred embodiment is a protein that has the amino acid sequence which is shown in FIG. 1, in SEQ ID NO:2 and disclosed as follows:

can determine whether such naturally occurring forms are mutant or polymorphic forms of MurD by sequence comparison. One can further determine whether the encoded protein, or fragments of any MurD protein, is biologically active by routine testing of the protein of fragment in a in vitro or in vivo assay for the biological activity of the MurD protein. For example, one can express N-terminal or C-terminal truncations, or internal additions or deletions, in host cells and test for their ability to catalyze the ATP-dependent addition of D-glutamate to an alanyl residue of the UDP-N-acetylmuramyl-L-alanine precursor.

It is known that there is a substantial amount of redundancy in the various codons which code for specific amino acids. Therefore, this invention is also directed to those DNA sequences encode RNA comprising alternative codons

```
MetSerLeuIleAlaSerAspHisPheArgIleValValGlyLeuGlyLysSerGlyMet  (SEQ ID NO:2)

SerLeuValArgTyrLeuAlaArgArgGlyLeuProPheAlaValValAspThrArgGlu

AsnProProGluLeuAlaThrLeuArgAlaGlnTyrProGlnValGluValArgCysGly

GluLeuAspAlaGluPheLeuCysSerAlaArgGluLeuTyrValSerProGlyLeuSer

LeuArgThrProAlaLeuValGlnAlaAlaAlaLysGlyValArgIleSerGlyAspIle

AspLeuPheAlaArgGlnAlaLysAlaProIleValAlaIleThrGlySerAsnAlaLys

SerThrValThrThrLeuValGlyGluMetAlaValAlaAlaAspLysArgValAlaVal

GlyGlyAsnLeuGlyThrProAlaLeuAspLeuLeuAlaAspAspIleGluLeuTyrVal

LeuGluLeuSerSerPheGlnLeuGluThrCysAspArgLeuAsnAlaGluValAlaThr

ValLeuAsnValSerGluAspHisMetAspArgTyrAspGlyMetAlaAspTyrHisLeu

AlaLysHisArgIlePheArgGlyAlaArgGlnValValValAsnArgAlaAspAlaLeu

ThrArgProLeuIleAlaAspThrValProCysTrpSerPheGlyLeuAsnLysProAsp

PheLysAlaPheGlyLeuIleGluGluAspGlyGlnLysTrpLeuAlaPheGlnPheAsp

LysLeuLeuProValGlyGluLeuLysIleArgGlyAlaHisAsnTyrSerAsnAlaLeu

AlaAlaLeuAlaLeuGlyHisAlaValGlyLeuProPheAspAlaMetLeuGlyAlaLeu

LysAlaPheSerGlyLeuAlaHisArgCysGlnTrpValArgGluArgGlnGlyValSer

TyrTyrAspAspSerLysAlaThrAsnValGlyAlaAlaLeuAlaAlaIleGluGlyLeu

GlyAlaAspIleAspGlyLysLeuValLeuLeuAlaGlyGlyAspGlyLysGlyAlaAsp

PheHisAspLeuArgGluProValAlaArgPheCysArgAlaValValLeuLeuGlyArg

AspAlaGlyLeuIleAlaGlnAlaLeuGlyAsnAlaValProLeuValArgValAlaThr

LeuAspGluAlaValArgGlnAlaAlaGluLeuAlaArgGluGlyAspAlaValLeuLeu

SerProAlaCysAlaSerLeuAspMetPheLysAsnPheGluGluArgGlyArgLeuPhe

AlaLysAlaValGluGluLeuAla
```

The present invention also relates to biologically active fragments and mutant or polymorphic forms of MurD polypeptide sequence as set forth as SEQ ID NO: 2, including but not limited to amino acid substitutions, deletions, additions, amino terminal truncations and carboxy-terminal truncations such that these mutations provide for proteins or protein fragments of diagnostic, therapeutic or prophylactic use and would be useful for screening for modulators, and/or inhibitors of MurD function.

Using the disclosure of polynucleotide and polypeptide sequences provided herein to isolate polynucleotides encoding naturally occurring forms of MurD, one of skill in the art which code for the eventual translation of the identical amino acid, as shown below:
A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=lsoleucine: codons AUA, AUC, AUU
K=Lys=Lysine: codons AAA, AAG
L=Leu=Leucine: codons UUA, UUG, CUA, CUC, CUG, CUU M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg-Arginine: codons AGA, AGG, CGA, CGC, CGG, CGU
S=Ser=Serine: codons AGC, AGU, UCA, UCC, UCG, UCU
T=Thr-Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU.

Therefore, the present invention discloses codon redundancy which can result in different DNA molecules encoding an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide. However, any given change can be examined for any effect on biological function by simply assaying for the ability to catalyze the ATP-dependent addition of D-glutamate to an alanyl residue of the UDP-N-acetylmuramyl-L-alanine precursor as compared to an unaltered MurD protein.

It is known that DNA sequences coding for a peptide can be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate.

As used herein, a "biologically active equivalent" or "functional derivative" of a wild-type MurD possesses a biological activity that is substantially similar to the biological activity of a wild type MurD. The term "functional derivative" is intended to include the "fragments," "mutants," "variants," "degenerate variants," "analogs," "orthologues," and "homologues" and "chemical derivatives" of a wild type MurD protein that can catalyze the ATP-dependent addition of D-glutamate to an alanyl residue of the UDP-N-acetylmuramyl-L-alanine precursor. The term "fragment" refers to any polypeptide subset of wild-type MurD. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the MurD or MurD functional derivative. The term "variant" refers to a molecule substantially similar in structure and function to either the entire wild-type protein or to a fragment thereof. A molecule is "substantially similar" to a wild-type MurD-like protein if both molecules have substantially similar structures or if both molecules possess similar biological activity. Therefore, if the two molecules possess substantially similar activity, they are considered to be variants even if the exact structure of one of the molecules is not found in the other or even if the two amino acid sequences are not identical. The term "analog" refers to a molecule substantially similar in function to either the full-length MurD protein or to a biologically active fragment thereof.

As used herein in reference to a MurD gene or encoded protein, a "polymorphic" MurD is a MurD that is naturally found in the population of Pseudomonads at large. A polymorphic form of MurD can be encoded by a different nucleotide sequence from the particular murD gene disclosed herein as SEQ ID NO:1. However, because of silent mutations, a polymorphic murD gene can encode the same or different amino acid sequence as that disclosed herein. Further, some polymorphic forms MurD will exhibit biological characteristics that distinguish the form from wild-type MurD activity, in which case the polymorphic form is also a mutant.

A protein or fragment thereof is considered purified or isolated when it is obtained at least partially free from it's natural environment in a composition or purity not found in nature. It is preferred that the molecule be present at a concentration at least about five-fold to ten-fold higher than that found in nature. A protein or fragment thereof is considered substantially pure if it is obtained at a concentration of at least about 100-fold higher than that found in nature. A protein or fragment thereof is considered essentially pure if it is obtained at a concentration of at least about 1000-fold higher than that found in nature. We most prefer proteins that have been purified to homogeneity, that is, at least 10,000–100,000 fold.

Probes and Primers

Polynucleotide probes comprising full length or partial sequences of SEQ ID NO:1 can be used to determine whether a cell or sample contains P. aeruginosa MurD DNA or RNA. The effect of modulators that effect the transcription of the murD gene can be studied via the use of these probes. A preferred probe is a single stranded antisense probe having at least the full length of the coding sequence of MurD. It is also preferred to use probes that have less than the full length sequence, and contain sequences specific for P. aeruginosa murD DNA or RNA. The identification of a sequence(s) for use as a specific probe is well known in the art and involves choosing a sequence(s) that is unique to the target sequence, or is specific thereto. It is preferred that polynucleotides that are probes have at least about 25 nucleotides, more preferably about 30 to 35 nucleotides. The longer probes are believed to be more specific for P. aeruginosa murD gene(s) and RNAs and can be used under more stringent hybridization conditions. Longer probes can be used but can be more difficult to prepare synthetically, or can result in lower yields from a synthesis. Examples of sequences that are useful as probes or primers for P. aeruginosa murD gene(s) are Primer A (sense) 5'-TTCTCGAGATGAGCCTGATCGCCTC-3'(SEQ ID NO:3) and Primer B (antisense) 5'-TTGGATCCTCACGCTAGCTCCTCTAC-3'(SEQ ID NO:4). These primers are nucleotides 51–67 (A) and the complement of nucleotides 1378–1395 (B) respectively, of SEQ ID NO:1. Restriction sites, underlined, for XhoI and BamHI are added to the 5' ends of the primers to allow cloning between the XhoI and BamHI sites of the expression vector pET-15b. However, one skilled in the art will recognize that these are only a few of the useful probe or primer sequences that can be derived from SEQ ID NO:1.

Polynucleotides having sequences that are unique or specific for P. aeruginosa murD can be used as primers in amplification reaction assays. These assays can be used in tissue typing as described herein. Additionally, amplification reactions employing primers derived from P. aeruginosa murD sequences can be used to obtain amplified P. aeruginosa murD DNA using the murD DNA of the cells as an initial template. The murD DNA so obtained can be a mutant or polymorphic form of P. aeruginosa murD that differs from SEQ ID NO:1 by one or more nucleotides of the MurD open reading frame or sequences flanking the ORF. The differences can be associated with a non-defective naturally occurring form or with a defective form of MurD. Thus, polynucleotides of this invention can be used in identification of various polymorphic *P. aeruginosa* murD genes or the detection of an organism having a *P. aeruginosa* murD gene. Many types of amplification reactions are known in the art and include, without limitation, Polymerase Chain Reaction, Reverse Transcriptase Polymerase Chain Reaction, Strand Displacement Amplification and Self-Sustained Sequence Reaction. Any of these or like reactions can be used with primers derived from SEQ ID NO:1.

Expression of MurD

A variety of expression vectors can be used to express recombinant MurD in host cells. Expression vectors are defined herein as nucleic acid sequences that include regulatory sequences for the transcription of cloned DNA and the translation of their mRNAs in an appropriate host. Such vectors can be used to express a bacterial gene in a variety of hosts such as bacteria, bluegreen algae, plant cells, insect cells and animal cells. Specifically designed vectors allow the shuttling of genes between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and regulatory sequences. A promoter is defined as a regulatory sequence that directs RNA polymerase to bind to DNA and initiate RNA synthesis. A strong promoter is one which causes mRNAs to be initiated at high frequency. Expression vectors can include, but are not limited to, cloning vectors, modified cloning vectors, specifically designed plasmids or viruses.

In particular, a variety of bacterial expression vectors can be used to express recombinant MurD in bacterial cells. Commercially available bacterial expression vectors which are suitable for recombinant MurD expression include, but are not limited to pQE (Qiagen), pET11a or pET15b (Novagen), lambda gt11 (Invitrogen), and pKK223-3 (Pharmacia).

Alternatively, one can express murD DNA in cell-free transcription-translation systems, or murD RNA in cell-free translation systems. Cell-free synthesis of MurD can be in batch or continuous formats known in the art.

One can also synthesize MurD chemically, although this method is not preferred.

A variety of host cells can be employed with expression vectors to synthesize MurD protein. These can include *E. coli*, *Bacillus*, and *Salmonella*. Insect and yeast cells can also be appropriate.

Following expression of MurD in a host cell, MurD polypeptides can be recovered. Several protein purification procedures are available and suitable for use. MurD protein and polypeptides can be purified from cell lysates and extracts, or from culture medium, by various combinations of, or individual application of methods including ultrafiltration, acid extraction, alcohol precipitation, salt fractionation, ionic exchange chromatography, phosphocellulose chromatography, lecithin chromatography, affinity (e.g., antibody or His-Ni) chromatography, size exclusion chromatography, hydroxylapatite adsorption chromatography and chromatography based on hydrophobic or hydrophillic interactions. In some instances, protein denaturation and refolding steps can be employed. High performance liquid chromatography (HPLC) and reversed phase HPLC can also be useful. Dialysis can be used to adjust the final buffer composition.

The MurD protein itself is useful in assays to identify compounds that modulate the activity of the protein— including compounds that inhibit the activity of the protein. The MurD protein is also useful for the generation of antibodies against the protein, structural studies of the protein, and structure/function relationships of the protein.

Modulators and Inhibitors of MurD

The present invention is also directed to methods for screening for compounds which modulate or inhibit a MurD protein. Compounds which modulate or inhibit MurD can be DNA, RNA, peptides, proteins, or non-proteinaceous organic or inorganic compounds or other types of molecules. Compounds that modulate the expression of DNA or RNA encoding MurD or are inhibitors of the biological function of MurD can be detected by a variety of assays. The assay can be a simple "yes/no" assay to determine whether there is a change in expression or function. The assay can be made quantitative by comparing the expression or function of a test sample with the levels of expression or function in a standard sample, that is, a control. A compound that is a modulator can be detected by measuring the amount of the MurD produced in the presence of the compound. An compound that is an inhibitor can be detected by measuring the specific activity of the MurD protein in the presence and absence of the compound.

The proteins, DNA molecules, RNA molecules and antibodies lend themselves to the formulation of kits suitable for the detection and anaysis of MurD. Such a kit would comprise a compartmentalized carrier suitable to hold in close confinement at least one container. The carrier would further comprise reagents such as recombinant MurD or anti-MurD antibodies suitable for detecting MurD. The carrier can also contain a means for detection such as labeled antigen or enzyme substrates or the like.

Pharmaceutical Compositions

Pharmaceutically useful compositions comprising a modulator or inhibitor of MurD can be formulated according to known methods such as by the admixture of a pharmaceutically acceptable carrier. Examples of such carriers and methods of formulation can be found in Remington's Pharmaceutical Sciences. To form a pharmaceutically acceptable composition suitable for effective administration, such compositions will contain an effective amount of the inhibitor.

Therapeutic, prophylactic or diagnostic compositions of the invention are administered to an individual in amounts sufficient to treat, prevent or diagnose disorders. The effective amount can vary according to a variety of factors such as the individual's condition, weight, sex and age. Other factors include the mode of administration. The appropriate amount can be determined by a skilled physician.

The pharmaceutical compositions can be provided to the individual by a variety of routes such as subcutaneous, topical, oral and intramuscular.

The term "chemical derivative" describes a molecule that contains additional chemical moieties which are not normally a part of the base molecule. Such moieties can improve the solubility, half-life, absorption, etc. of the base molecule. Alternatively the moieties can attenuate undesirable side effects of the base molecule or decrease the toxicity of the base molecule. Examples of such moieties are described in a variety of texts, such as Remington's Pharmaceutical Sciences.

Compounds identified according to the methods disclosed herein can be used alone at appropriate dosages. Alternatively, co-administration or sequential administration of other agents can be desirable.

The present invention also provides a means to obtain suitable topical, oral, systemic and parenteral pharmaceutical formulations for use in the methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they can also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention can be administered in a single daily dose, or the total daily dosage can be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are presented by the way of illustration and, because various other embodiments will be apparent to those in the art, the following is not to be construed as a limitation on the scope of the invention. For example, while particular preferred embodiments of the invention are presented herein, it is within the ability of persons of ordinary skill in the art to modify or substitute vectors, host cells, compositions, etc., or to modify or design protocols or assays, all of which may reach the same or equivalent performance or results as the embodiments shown herein.

EXAMPLE 1
General Materials and Methods
All reagents were purchased from Sigma Chemical Co, SL Louis, Mo., unless otherwise indicated. UDP-N-acetylmuramyl-L-alanine was synthesized and purified by a method known in the art (Jin, H., Emanuele, J. J., Jr., Fairman, R., Robertson, J. G., Hail, M. E., Ho, H.-T., Falk, P. and Villafranca, J. J, 1996. Structural studies of *Escherichia coli* UDP-N-acetylmuramate: L-alanine ligase, Biochemistry 35: 14423–14431).

DNA manipulations reagents and techniques. Restriction endonucleases and T4 ligase were obtained from Gibco-BRL. Agarose gel electrophoresis and plasmid DNA preparations were performed according to published procedures (Sambrook, J., E. F. Fritsch, and T. Maniatis, 1989, Molecular cloning: a L, Laboratory Manual, 2nd ed. Cold Spring Harbor, N.Y.: Cold Spring Harbor Laboratory). Recombinant plasmids containing *P. aeruginosa* murD were propagated in *E. coli* DH5a (Gibco-BRL, Rockville, Md.) prior to protein expression in *E. coli* BL21 (DE3)/plysS (Novagen, Madison, Wis.). SDS-PAGE was performed with precast gels (Novagen). DNA sequences were determined using an automated ABI PRISM™ DNA sequencer (Perkin-Elmer ABI, Foster City, Calif.).

EXAMPLE 2
Cloning of *Pseudomonas aeruginosa* murD
Genomic DNA from *P. aeruginosa* (strain MB4439) was prepared from 100 ml late stationary phase culture in Brain Heart Infusion broth (Difco, Detroit, Mich.). Cells were washed with 0.2 M sodium acetate, suspended in 10 ml of TEG (100 mM Tris, pH 7, containing 10 mM EDTA and 25% glucose) and lysed by incubation with 200 $\mu$g of N-acetylmuramidase (Sigma) for 1 h at 37° C. Chromosomal DNA was purified from the cell lysate using a Qiagen (Santa Clarita, Calif.) genomic DNA preparation kit and following the manufacturers protocol. Briefly, the cell lysate was treated with protease K at 50° C. for 45 min, loaded onto an equilibrated Qiagen genomic tip, entered into the resin by centrifugation at 3000 rpm for 2 min. Following washing the genomic tip, the genomic DNA was eluted in distilled water and kept at 4° C. Approximately 50 ng genomic DNA was used as a template in PCR reactions to clone murD.

Two oligonucleotide primers (Gibco/BRL, Bethesda, Md.) complementary to sequences at the 5' and the 3' ends of *P. aeruginosa* murD were used to clone this gene using KLENTAQ ADVANTAGE™ polymerase (Clontech, Palo Alto, Calif.). The primer nucleotide sequences were as follows: 5'-TCTCGAGATGAGCCTGATCGCCTC-3' (SEQ ID NO:3) (a XhoI linker plus nucleotides 51–67 of SEQ ID NO: 1), and 5'-TTGGATCCTCACGCTAGCTCCTCTAC-3' (SEQ ID NO:4) (a BamHI linker plus the complement of nucleotides 1378–1395 of SEQ ID NO: 1). A PCR product representing *P. aeruginosa* murD was verified by nucleotide sequence, digested with XhoI and BamHI, and cloned between the XhoI and BamHI sites of pET-15b, creating plasmid pPaeMurD. This plasmid was used for expression of the murD gene in *E. coli*.

The plasmid pPaeMurD has been deposited with the American Type Culture Collection on Apr. 17, 1998, under the terms of the Budapest Treaty for the Deposit of Microorganisms and has been designated as ATCC 98745. The deposited material is provided as a convenience and is not an indication that the deposited material is required to describe or practice the invention. The sequence of the polynucleotide of the deposit, and the encoded amino acid sequence, are incorporated herein by reference and are controlling in the event of a conflict with any description of the sequences provided in this specification or the associated drawings. A license may be required to make, use, sell or offer to sell the polynucleotide of the deposit or a protein of the amino acid sequence encoded by the polynucleotide. No such license is granted herein.

EXAMPLE 3
Sequence Analysis of *Pseudomonas aeruginosa* murD
The nucleotide sequence of murD, determined in both orientations, and the deduced amino acid sequence of the MurD protein is depicted in FIG. 1. Sequence comparison using the BLAST (1) algorithm against the GenBank data-base showed that, to varying degrees, the cloned region is homologous (68% similar, 53% identical) to murD gene from E. coli (Mengin-Lecreulx, D. and J. van Heijenoort, 1990, Nucleotide sequence of the murD gene encoding the UDP-MurNAc-L-Ala-D-Glu synthetase of Escherichia coli. Nucleic Acids Research 18:183).

Multiple sequence alignments of MurC (Ikeda, M., M. Wachi, H. K. Jung, F. Ishino, and M. Matsuhashi, 1990b. Nucleotide sequence involving murG and murC in the mra gene cluster of Escherichia coli. Nucleic Acids Res. 18:4014), MurD, MurE (Tao, J. S, and E. E., Ishiguro, 1989. Nucleotide sequence of the murE gene of Escherichia coli. Can. J. Microbiol. 35:1051–1054), and MurF (Parquet, C., D., Mengin-Lecreulx, B. Flouret, D. Mengin-Lecreulx, and J. van Heijenoort, 1989. Nucleotide sequence of the murF gene encoding the UDP-MurNAc-pentapeptide synthetase of Escherichia coli., Nucleic Acids Res. 17:5379) proteins from several bacterial genera revealed four regions of homology with certain residues conserved amongst Mur ligases of both Gram-positive and Gram-negative bacteria (Eveland, S. S., D. L. Pompliano, and M. S. Anderson, 1997. Conditionally lethal Escherichia coli murein mutants contain point defects that map to regions conserved among murein and folyl poly-g-glutamate ligases: Identification of a ligase superfamily. Biochemistry, 36: 6223–6229, Ikeda, M., M. Wachi, H. K. Jung, F. Ishino, and M. Matsuhashi, 1990c. Homology among MurC, MurD, MurE and MurF proteins in Escherichia coli and that between E. coli murG and a possible murg protein in Bacillus subtilis. J. Gen. Appl. Microbiol. 36: 179–187). The homologous regions may correlate with the catalytic functions of these enzymes (Eveland, et al., 1997). Most notable is the putative ATP binding region I that was found in MurF (Parquet, C., D., et al., 1989.) and is also conserved in P. aeruginosa MurD protein GlySerAspGlyLysThrThr (codons 116 to 122, SEQ ID NO:2). While region I is an ATP-binding domain (Ikeda, et al., 1990), the functions of the other homologous regions is unknown. All four homologous regions are conserved in the P. aeruginosa MurD.

EXAMPLE 4

Overexpression, Purification and Enzymatic Activity of Pseudomonas aeruginosa MurD murD was cloned into the expression vector pET-15b (Novagen) as described above to create plasmid pPaeMurD. The pET-15b vector incorporates the 6× Histidine-tag into the protein construct to allow rapid purification of MurD by affinity chromatography. The pET (Plasmids for Expression by T7 RNA polymerase) plasmids are derived from pBR322 and designed for protein over-production in E. coli. The vector pET-15b contains the ampicillin resistance gene, ColE1 origin of replication in addition to T7 phage promoter and terminator. The T7 promoter is recognized by the phage T7 RNA polymerase but not by the E. coli RNA polymerase. A host E. coli strain such as BL21 (DE3)pLysS is engineered to contain integrated copies of T7 RNA polymerase under the control of lacUV5 that is inducible by IPTG. Production of a recombinant protein in the E. coli strain BL21 (DE3) pLysS occurs after expression of T7RNA polymerase is induced.

The pPaeMurD plasmid was introduced into the host strain BUI DE3/pLysS (Novagen) for expression of His-tagged MurD. Colonies were grown at 37° C. in 100 ml of LB broth containing 100 mg/ml ampicillin and 32 µg/ml chloramphenicol. When cultures reached a cell density of $A_{600}$=0.5, cells were pelleted and then resuspended in M9ZB medium (Novagen) containing 1 mM IPTG. Cells were induced for 3 h at 30° C., pelleted at 3000 g, and frozen at −80° C.

Cultures containing either the recombinant plasmid pPae-MurD or the control plasmid vector, pET-15b were grown at 30° C. and induced with IPTG. Cells transformed with pPaeMurD contained an inducible protein of approximately 51 kDa, corresponding to the expected size of P. aeruginosa MurD protein as shown by SDS-PAGE. There were no comparable detectable protein bands after induction of cells transformed with the control plasmid vector, pET-15b.

Purification of Recombinant MurD Enzyme.

The cell pellet from 100 ml of induced culture prepared as described above was resuspended in 10 ml BT buffer (50 mM bis-tris-propane, pH 8.0, containing 100 mM potassium chloride and 1% glycerol) at 4° C. Cells were lysed either by freeze-thaw or by French Press. After centrifugation, the supernatant was mixed with 15 ml of freshly prepared TALON™ (Clontech) resin and incubated for 30 min at room temp. The resin was washed twice by centrifugation with 25 ml of BT buffer at room temperature. Finally, the resin was loaded into a column and washed with 20 ml of BT, pH 7.0, containing 5 mM imidazole. Protein was eluted with 20 ml of BT buffer pH 8.0, containing 100 mM imidazole. Fractions (0.5 ml) were collected and analyzed by SDS-Gel electrophoresis. This resulted in a partially purified preparation of P. aeruginosa MurD protein that could be used in activity assays. The protein may be purified further, if desired, using methods known in the art.

Assay for Activity of MurD Enzyme.

The ATP-dependent MurD activity was assayed by monitoring the formation of product ADP using the pyruvate kinase and lactate dehydrogenase coupled enzyme assay. The reaction was monitored spectrophotometrically.

Typically, the assay contained 100 mM BIS-TRIS-propane, pH 8.0, 200 µM NADH, 1 mM ATP, 20 mM PEP, 5 mM $MgCl_2$, 1 mM DTT, 350 µM UDP-N-acetyl-muramyl-L-alanine, 1 mM D-glutamate, 33 units/ml of pyruvate kinase and 1660 units/ml of lactate dehydrogenase in a final volume of 200 or 400 µl. The mixture was incubated at 25° C. for 5 min and the reaction initiated by the addition of 1–10 µg of MurD. These conditions are one example of an assay useful for evaluating the activity of MurD. Other assays can be used, or amounts of buffers, substrate and enzyme can be changed, as desired, to alter the rate of production of ADP.

ADP formation was monitored by the decrease in absorbance at 340 nm as a function of time using a Molecular Devices SPECTRAMAXPLUS™ microtiterplate spectrophotomer (for 200 µl assays) or a Hewlett-Packard HP8452A spectrophotometer equipped with a circulating water bath (for 400 µl assays). Rates were calculated from the linear portions of the progress curves using the extinction coefficient for NADH, e=6220 $cm^{-1}$ $M^{-1}$. One unit of MurD activity is equal to 1 µmol of ADP formed per min at 25° C. MurD activity co-eluted with a ~51 kDa protein.

TABLE 1

Specific activities of recombinant MurD from E. coli and P. aeruginosa.

| Species | protein used (mg) | units (µmole/min)[1] | Specific activity ((µmol/min)/mg) |
|---|---|---|---|
| E. coli[2] | 0.0025 | 0.00512 | 2.12 |
| P. aeruginosa[3] | 0.0015 | 0.0047 | 3.12 |

[1]Concentration of UDP-N-acetylmuramyl-L-ala, D-glutamate, ATP were 350 µM, 1 mM, and 1 mM, respectively. Volume of the reactions were 200 µl at 25° C.
[2]E. coli Mur D was prepared described in Pratviel-Sosa, et al. (1991).
[3]P. aeruginosa MurD was partially purified as described above.

Assays have been conducted using 120 and 350 µM UDP-N-acetyl-muramyl-L-alanine. However, it has been observed that at the higher level of 350 µM UDP-N-acetyl-muramyl-L-alanine, substrate inhibition of the E. coli MurD occurs. At the lower level, the specific activity of the *E. coli* enzyme can be in the area of 8 units/mg. It is unclear whether the *P. aeruginosa* enzyme is similarly inhibited.

EXAMPLE 5
Screening for Inhibitors of MurD

One assay for the measurement of the activity of MurD is provided in Example 4. That assay, and other assays for MurD activity can be adapted for screening assays to detect inhibitors of MurD. For example, for inhibition assays, inhibitors in DMSO are added at the desired concentration to the assay mixture. In a separate, control reaction, only DMSO is added to the assay mixture. The reactions are initiated by the addition of enzyme (MurD). Rates are calculated as described above. Relative activities are calculated from the equation 1:

$$\text{relative activity} = \text{rate with inhibitor/rate without inhibitor.} \quad (1)$$

Inhibition constant (IC50) values are determined from a range of inhibitor concentrations and calculated from equation 2.

$$\text{relative activity} = 1/(1+[I]/IC50) \quad (2)$$

One can use computer software to assist in the analysis, e.g., SIGMA PLOT™ (Jandel Scientific).

We prefer inhibitors of MurD that result in relative activities of the MurD enzyme of at least less than 75%, more preferably, 25–50% or 10–25%. We most prefer inhibitors resulting in relative activities of less than 20%, particularly less than 10% of the activity of Mur D in the absence of the inhibitor.

We also prefer inhibitors that effectively lower the relative activity of MurD when the inhibitor is present at a very low concentration.

EXAMPLE 8
Therapy Using Inhibitors of MurD

A patient presenting with an indication of infection with a microorganism susceptible to inhibitors of MurD, e.g., gram positive and negative bacteria, including *P. aeruginosa*, can be treated by administration of inhibitors of MurD. Physicians skilled in the art are familiar with administering therapeutically effective amounts of inhibitors or modulators of microbial enzymes. Such skilled persons can readily determine an appropriate dosing scheme to achieve a desired therapeutic effect.

Therapy can also be prophylactic. For example, a patient at risk for developing a bacterial infection, including infection with *P. aeruginosa*, can be treated by administration of inhibitors of MurD. Physicians skilled in the art are familiar with administering therapeutically effective amounts of inhibitors or modulators of microbial enzymes. Such skilled persons can readily determine an appropriate dosing scheme to achieve a desired therapeutic effect.

---

What is claimed is:

1. An isolated and purified polynucleotide selected from the group consisting of:
   (a) a polynucleotide encoding a polypeptide having the amino acid sequence of SEQ ID NO: 2, and
   (b) a polynucleotide which is fully complementary to the polynucleotide of (a).

2. The polynucleotide of claim 1 wherein the polynucleotide encoding a polypeptide having the amino acid sequence of SEQ ID NO: 2 comprises the nucleotide sequence of SEQ ID NO:1.

3. An isolated and purified polynucleotide that is an expression vector comprising a polynucleotide of claim 1.

4. A host cell comprising the heterologous expression vector of claim 3.

5. A process for expressing a polypeptide having the amino acid sequence of SEQ ID NO: 2 in a recombinant host cell, comprising:
   (a) transforming a host cell with an expression vector of claim 3; and,
   (b) culturing the host cell of step (a) in conditions under which allow expression of said polypeptide from said expression vector.

* * * * *